(12) United States Patent
Ishikawa et al.

(10) Patent No.: US 7,090,998 B2
(45) Date of Patent: Aug. 15, 2006

(54) METHOD FOR PRODUCING TARGET SUBSTANCE BY FERMENTATION

(75) Inventors: Yukiko Ishikawa, Kawasaki (JP); Akira Imaizumi, Kawasaki (JP); Kazuhiko Matsui, Kawasaki (JP); Hiroyuki Kojima, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/613,990

(22) Filed: Jul. 8, 2003

(65) Prior Publication Data
US 2004/0180404 A1  Sep. 16, 2004

(30) Foreign Application Priority Data
Jul. 12, 2002  (JP)  ............................. 2002-203764

(51) Int. Cl.
*C12P 1/04* (2006.01)
*C12N 1/20* (2006.01)

(52) U.S. Cl. .................. 435/41; 435/252.3; 435/252.8

(58) Field of Classification Search ............. 435/252.1, 435/252.8, 253.3
See application file for complete search history.

(56) References Cited

U.S. PATENT DOCUMENTS

| | | | |
|---|---|---|---|
| 5,919,694 A * | 7/1999 | Sugimoto et al. | 435/252.33 |
| 6,040,160 A | 3/2000 | Kojima et al. | |
| 2002/0155556 A1 | 10/2002 | Imaizumi et al. | 435/115 |
| 2004/0152174 A1 | 8/2004 | Cervin et al. | 435/106 |
| 2004/0229305 A1 | 11/2004 | Usuda et al. | 435/69.1 |

FOREIGN PATENT DOCUMENTS

WO  WO 2004/033421  4/2004

OTHER PUBLICATIONS

Search Report from EPO, Nov. 13, 2003, EPO.

Cotter et al., "Contribution of the fnr and arcA gene products in coordinate regulation of cytochrome o and d oxidase (cyoABCDE and cydAB) genes in *Escherichia coli*" FEMS Micro. Lett., 91:31-36 (1992).

Iuchi et al., "arcA (dye), a global regulatory gene in *Escherichia coli* mediating repression of enzymes in aerobic pathways" Proc. Natl. Acad. Sci. USA, 85:1888-1892 (1988).

Nystrom et al., "Bacterial defense against aging: role of the *Escherichia coli* ArcA regulator in gene expression, readjusted energy flux and survival during stasis" EMBO J. 15: 3219-3228 (1996).

Database WPI, Section Ch, Week 200114, Derwent Pub, London, AN 2001-138133, XP002260035 & WP01/02544A (Jan. 11, 2001).

Database WPI, Section Ch, Week 200114, Derwent Pub, London, AN 2001-138135, XP002260036 & WO01/02546A (Jan. 11, 2001).

S. Iuchi, et al., Cell, Minireview, vol. 66, pp. 5-7, "Adaptation of *Escherichia coli* to Respiratory Conditions: Regulation of Gene Expression", Jul. 12, 1991.

F. R. Blattner, et al., Science, vol. 277, pp. 1453-1462, "The Complete Genome Sequence of *Escherichia coli* K-12", Sep. 5, 1997.

* cited by examiner

*Primary Examiner*—Nancy Vogel

(74) *Attorney, Agent, or Firm*—Cermak & Kenealy, LLP; Shelly Guest Cermak

(57) ABSTRACT

In a method for producing a target substance utilizing a microorganism, which comprises culturing a γ-proteobacterium in a medium to produce and accumulate the target substance in the medium or cells and collecting the target substance, there is used a strain in which the ArcA protein does not normally function in the cell by means of, for example, disruption of the arcA gene on the chromosome.

8 Claims, 1 Drawing Sheet

METHOD FOR PRODUCING TARGET SUBSTANCE BY FERMENTATION

FIELD OF THE INVENTION

The present invention relates to a technique used in the fermentation industry, more precisely, a method for efficiently producing a target substance such as L-amino acids by fermentation utilizing a microorganism.

DESCRIPTION OF THE RELATED ART

Bacterial cells have been modifying their metabolic pathways, respiratory pathways and so forth in order to adapt to various environments. In the energy metabolism, Arc (aerobic respiration control) and Fnr (fumarate nitrate reduction) are known as control systems playing important roles. These consist of global regulator proteins and universally existing in *E. coli* and other analogous species. The former is encoded by the arcA gene existing at the position of 0 minute of the *E. coli* chromosome, the latter is encoded by the fnr gene existing at the position of 29 minutes of the *E. coli* chromosome, and the both adapt the cell to an environment by controlling many factors under an anaerobic condition. Moreover, it has been elucidated that the ArcA protein and the Fnr protein are transcription factors, and they positively or negatively control expression of a target gene on the *E. coli* chromosome under an anaerobic condition by directly binding to a promoter region of the target gene (S. Iuchi et al., Cell, 66, 5–7 (1991)).

Recently, expression profiles of strains in which genes coding global regulators such as the ArcA protein and Fnr protein derived from *E. coli* are disrupted are collected in a database by using DNA microarray techniques and opened to the public (genome.ad.jp).

So far, it is known that the ArcA protein negatively controls expression of the genes for the tricarboxylic acid cycle (S. Iuchi et al., Cell, 66, 5–7 (1991)), and the expression of the genes for the tricarboxylic acid cycle is increased in the arcA-disrupted strain in the database. On the other hand, it is known that the Fnr protein positively controls gene expression for the respiratory pathway that functions under an anaerobic condition.

As for the expression profiles in the global factor-disrupted strains, the dam-disrupted strain can be mentioned as a strain in which gene expression for the TCA is increased like the arcA-disrupted strain (H. Mori, Nara Institute of Science and Technology, oral announcement at the symposium "Green Biotechnology of Genome Age", 2001, organized by Japan Bioindustry Association, Resource Biotransformation Study Group).

The Dam protein is a methylase for modification factors involved in intracellular restriction modification systems, and it is encoded by the dam gene existing at the position of 76 minutes of the *E. coli* chromosome (Proc. Natl. Acad. Sci. U.S.A., 87 (23), 9454–9458 (1990)).

It has not been reported so far about improvement of substance production through expression control of the global factors such as genes arcA, fnr and dam.

Description of the Related Art

An object of the present invention is to improve production efficiency in production of a useful substance by fermentation utilizing a γ-proteobacterium such as *Escherichia* bacteria.

The inventors of the present invention conducted various researches in order to achieve the aforementioned object, and they found production of substance by a γ-proteobacterium could be improved by modifying a gene coding for a regulator protein universally existing in γ-proteobacteria. That is, they found that an ability to produce a target substance could be improved by disrupting the arcA gene in a γ-proteobacterium and thus accomplished the present invention.

That is, the present invention provides followings.

(1) A γ-proteobacterium having an ability to produce a target substance and modified so that an ArcA protein does not normally function.

(2) The γ-proteobacterium according to (1), wherein the ArcA protein that normally functions is a protein defined in the following (A) or (B):

(A) a protein having the amino acid sequence of SEQ ID NO: 32;

(B) a protein having the amino acid sequence of SEQ ID NO: 32 including substitution, deletion, insertion or addition of one or several amino acids and improving an ability to produce a target substance when the protein does not normally function in the γ-proteobacterium compared with the case where the protein normally functions.

(3) The γ-proteobacterium according to (1), wherein the ArcA protein that normally functions is a protein having 70% or more of homology to the amino acid sequence of SEQ ID NO: 32 and improving an ability to produce a target substance when the protein does not normally function in the γ-proteobacterium compared with the case where the protein normally functions.

(4) The γ-proteobacterium according to (1), wherein the ArcA protein that normally functions is a protein having the amino acid sequence of SEQ ID NO: 32 including substitution, deletion, insertion or addition of 2 to 20 amino acids and improving an ability to produce a target substance when the protein does not normally function in the γ-proteobacterium compared with the case where the protein normally functions.

(5) The γ-proteobacterium according to any one of (1) to (4), wherein the ArcA protein does not normally function by means of disruption of an arcA gene on a chromosome.

(6) The γ-proteobacterium according to (5), wherein the arcA gene is DNA defined in the following (a) or (b):

(a) DNA containing the nucleotide sequence of the nucleotide numbers 101 to 817 of SEQ ID NO: 31;

(b) DNA hybridizable with the nucleotide sequence of the nucleotide numbers 101 to 817 of SEQ ID NO: 31 or a probe that can be produced from the nucleotide sequence under the stringent condition and coding for a protein that improves an ability to produce a target substance when the protein does not normally function compared with the case where the protein normally functions.

(7) The γ-proteobacterium according to any one of (1) to (6), which is a bacterium belonging to the genus *Escherichia*.

(8) The γ-proteobacterium according to any one of (1) to (7), wherein the target substance is an L-amino acid.

(9) The γ-proteobacterium according to (8), wherein the L-amino acid is selected from the group consisting of L-lysine, L-glutamic acid and L-arginine.

(10) A method for producing a target substance, which comprises culturing the γ-proteobacterium according to any one of (1) to (9) in a medium to produce and accumulate the target substance in the medium or cells and collecting the target substance from the medium or cells.

According to the present invention, when a useful substance such as L-amino acids is produced by using a γ-proteobacterium, the production efficiency can be improved.

DETAILED EXPLANATION OF THE INVENTION

Figure 1:
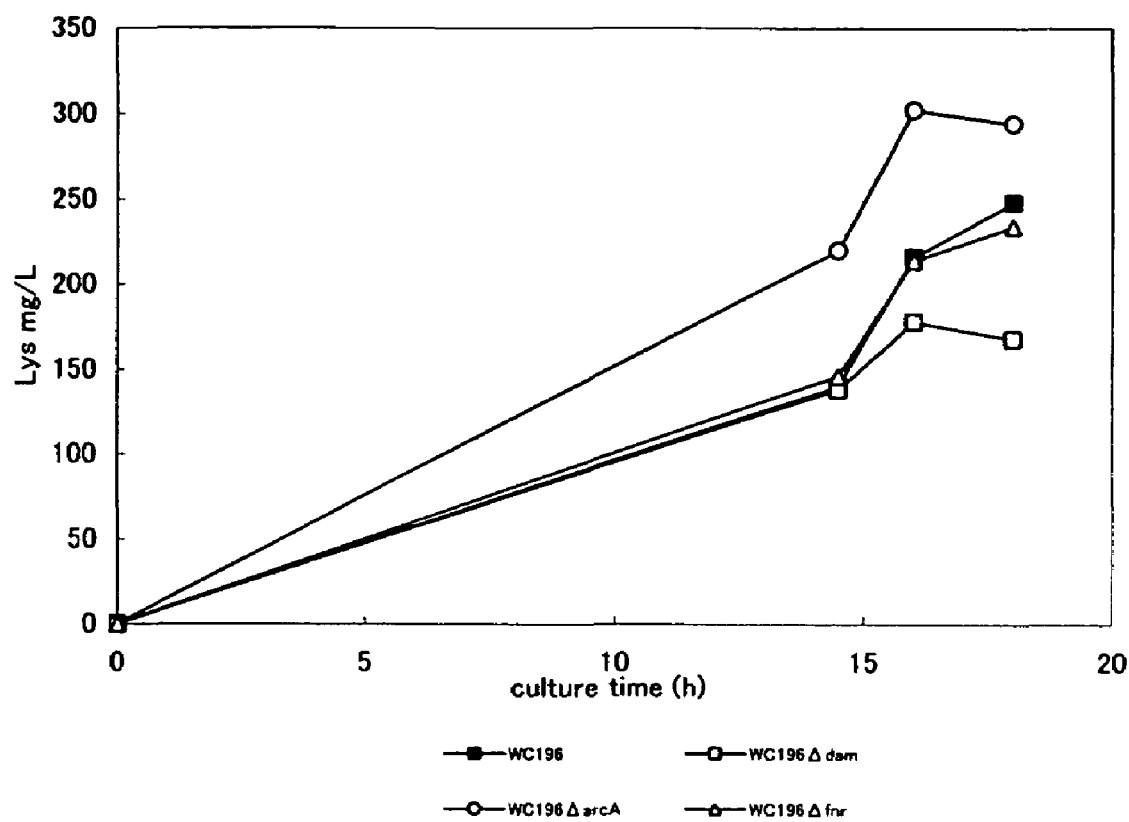
FIG. 1 shows accumulation patterns in WC196, WC196ΔarcA, WC196Δdam and WC196Δfnr.

Hereafter, the present invention will be explained in detail.

<1> γ-Proteobacterium of the Present Invention

The γ-proteobacterium used for the present invention is not particularly limited so long as it is a microorganism belonging to γ-proteobacteria such as genus *Escherichia, Enterobacter, Pantoea, Klebsiella, Serratia, Erwinia, Salmonella, Morganella* or the like and has an ability to produce a target substance. Specifically, those classified into the γ-proteobacteria according to the taxonomy used in the NCBI (National Center for Biotechnology Information) database can be used.

Examples of the bacterium belonging to the genus *Escherichia* include *E. coli* and so forth. Examples of the belonging to the genus *Enterobacter* include *Enterobacter agglomerans, Enterobacter aerogenes* and so forth.

There are some species of *Enterobacter agglomerans* recently re-classified into *Pantoea agglomerans, Pantoea ananatis, Pantoea stewartii agglomerans* or the like based on nucleotide sequence analysis of 16S rRNA etc. In the present invention, the bacterium may belong to either the genus *Enterobacter* or *Pantoea* so long as it is classified into γ-proteobacteria and has the arcA gene.

When *E. coli* is bred by using genetic engineering techniques, the *E. coli* K12 strain and derivatives thereof can be used. Further, when *Pantoea ananatis* is bred by using genetic engineering techniques, *Pantoea ananatis* strains AJ13355 (FERM BP-6614), AJ13356 (FERM BP-6615) and AJ13601 (FERM BP-7207), and derivatives thereof can be used. Although the above-mentioned strains were identified as *Enterobacter agglomerans* when they were isolated, these strains has been re-classified into *Pantoea ananatis* based on nucleotide sequence analysis of 16S rRNA etc. as described above.

The γ-proteobacterium of the present invention is any one of the aforementioned bacteria, and is a bacterium having an ability to produce a target substance. The "ability to produce a target substance" means an ability to produce and accumulate the target substance in cells or a medium in such a degree that, when the bacterium of the present invention is cultured in the medium, the target substance can be collected from the cells or medium.

The target substance to be produced according to the present invention is not particularly limited, so long as it is a substance that is produced by a γ-proteobacterium and synthesized via the tricarboxylic acid cycle or a substance synthesized from such a substance as a substrate. Examples include, for example, those conventionally produced by γ-proteobacteria, i.e., various amino acids such as L-lysine, L-threonine, L-isoleucine, L-glutamic acid, L-glutamine and L-arginine, organic acids such as L-homoserine and succinic acid and so forth. Further, the present invention can also be applied to a substance that has not so far been industrially produced by using γ-proteobacteria, so long as it can be synthesized from a substance synthesized via the TCA cycle as a substrate.

As L-lysine producing γ-proteobacteria, there can be exemplified mutants having resistance to an L-lysine analogue. This L-lysine analogue is a substance that inhibits growth of L-amino acid producing strain, but this inhibition is fully or partially canceled when L-lysine coexists in a medium. Examples of the L-lysine analogue include oxalysine, lysine hydroxamate, S-(2-aminoethyl)-L-cysteine (AEC), γ-methyllysine, α-chlorocaprolactam and so forth. Mutants having resistance to these lysine analogues can be obtained by subjecting γ-proteobacteria to a conventional artificial mutagenesis treatment. Specific examples of bacterial strain used for producing L-lysine include *E. coli* AJ11442 (FERM BP-1543, NRRL B-12185; refer to Japanese Patent Laid-open Publication (Kokai) No. 56-18596 and U.S. Pat. No. 4,346,170) and *E. coli* VL611. In these microorganisms, feedback inhibition of aspartokinase by L-lysine is desensitized.

In addition to the above, there can be mentioned, for example, L-threonine producing bacteria described later, because inhibition of aspartokinase by L-lysine is generally eliminated also in L-threonine producing bacteria.

In the Examples described later, the WC196 strain was used as an L-lysine producing bacterium of *E. coli*. This bacterial strain was bred by imparting AEC resistance to the W3110 strain derived from *E. coli* K-12. This strain was designated as the *E. coli* AJ13069, and was deposited at the National Institute of Bioscience and Human-Technology, Agency of Industrial Science and Technology (presently, the independent administrative corporation, International Patent Organism Depositary, National Institute of Advanced Industrial Science and Technology, postal code: 305-8566, Chuo Dai-6, 1-1 Higashi 1-Chome, Tsukuba-shi, Ibaraki-ken, Japan) on Dec. 6, 1994 and received an accession number of FERM P-14690. Then, it was converted to an international deposit under the provisions of the Budapest Treaty on Sep. 29, 1995, and received an accession number of FERM BP-5252 (refer to International Patent Publication WO96/17930).

Examples of L-threonine producing γ-proteobacteria include *E. coli* VKPM B-3996 (RIA 1867, refer to U.S. Pat. No. 5,175,107), strain MG442 (refer to Gusyatiner et al., Genetika (in Russian), 14, pp. 947–956, 1978) and so forth.

Examples of the microorganism belonging to γ-proteobacteria and having L-glutamic acid producing ability include, for example, microorganisms deficient in α-ketoglutarate dehydrogenase activity or having reduced α-ketoglutarate dehydrogenase activity. Bacteria belonging to the genus *Escherichia* deficient in α-ketoglutarate dehydrogenase activity or having reduced α-ketoglutarate dehydrogenase activity and methods for obtaining them are described in Japanese Patent Laid-open Publication (Kokai) Nos. 5-244970 and 7-203980. Specifically, the following strains can be mentioned.

*E. coli* W3110sucA::KM$^r$
*E. coli* AJ12624 (FERM BP-3853)
*E. coli* AJ12628 (FERM BP-3854)
*E. coli* AJ12949 (FERM BP-4881)

*E. coli* W3110sucA::Km$^r$ is a strain obtained by disrupting the α-ketoglutarate dehydrogenase gene (hereinafter referred to as "sucA gene") of *E. coli* W3110, and it is a strain completely deficient in the α-ketoglutarate dehydrogenase.

Microorganisms belonging to γ-proteobacteria and deficient in α-ketoglutarate dehydrogenase activity or having reduced α-ketoglutarate dehydrogenase activity and methods for obtaining them are described in Japanese Patent Laid-open Publication (Kokai) Nos. 5-244970 and 7-203980.

Examples of L-arginine producing γ-proteobacteria include *E. coli* into which argA gene has been introduced (Japanese Patent Laid-Open Publication No. 57-5693) and *E. coli* strain 237 (Russian Patent No. 200117677) or the like.

Examples of L-isoleucine producing γ-proteobacteria include *E. coli* KX141 (VKPM B-4781, refer to European Patent Laid-open Publication No. 519,113).

Examples of L-homoserine producing Escherichia bacteria include the NZ10 strain, which is a Leu+ revertant of the C600 strain (refer to Appleyard R. K., Genetics, 39, pp. 440–452, 1954).

As succinic acid producing γ-proteobacteria, examples using *E. coli* are known (Wang, X., et al., Appl. Biochem. Biotech., 70–72, 919–928 (1998)).

Further, bacteria belonging to the genus *Escherichia* having L-amino acid producing ability can also be bred by introducing DNA having genetic information involved in biosynthesis of L-amino acids and enhancing the ability utilizing a gene recombination technique. For example, as for L-lysine producing bacteria, examples of genes that can be introduced include, for example, genes coding for enzymes of the biosynthetic pathway of L-lysine such as phosphoenolpyruvate carboxylase, aspartokinase, dihydrodipicolinate synthetase, dihydrodipicolinate reductase, succinyldiaminopimelate transaminase and succinyldiaminopimelate deacylase. In case of a gene of an enzyme suffering from feedback inhibition by L-aspartic acid or L-lysine such as phosphoenolpyruvate carboxylase or aspartokinase and dihydrodipicolinate synthetase, it is desirable to use a mutant gene coding for an enzyme in which such inhibition is eliminated.

Further, as for L-glutamic acid producing bacteria, examples of genes that can be introduced include genes of glutamate dehydrogenase, glutamine synthetase, glutamate synthase, isocitrate dehydrogenase, aconitate hydratase, citrate synthase, phosphoenolpyruvate carboxylase, pyruvate dehydrogenase, pyruvate kinase, phosphoenolpyruvate synthase, enolase, phosphoglyceromutase, phosphoglycerate kinase, glyceraldehyde-3-phosphate dehydrogenase, triose phosphate isomerase, fructose bis-phosphate aldolase, phosphofructokinase, glucose phosphate isomerase and so forth.

Further, an activity of an enzyme that catalyzes a reaction for producing a compound other than the target L-amino acid by branching off from the biosynthetic pathway of the L-amino acid may be decreased or made deficient. For example, examples of such an enzyme that catalyzes a reaction for producing a compound other than L-lysine by branching off from the biosynthetic pathway of L-lysine include homoserine dehydrogenase (refer to International Patent Publication WO95/23864). Further, examples of an enzyme that catalyzes a reaction for producing a compound other than L-glutamic acid by branching off from the biosynthetic pathway of L-glutamic acid include α-ketoglutarate dehydrogenase, isocitrate lyase, phosphate acetyltransferase, acetate kinase, acetohydroxy acid synthase, acetolactate synthase, formate acetyltransferase, lactate dehydrogenase, glutamate decarboxylase, 1-pyrophosphate dehydrogenase and so forth.

In breeding of γ-proteobacteria having such a target substance producing ability as mentioned above, to introduce a gene into γ-proteobacteria to enhance their ability, there can be used a method in which a vector autonomously replicable in a γ-proteobacterium cell is ligated to the gene to produce recombinant DNA and γ-proteobacterium is transformed with it. In addition, it is also possible to incorporate a target gene into host chromosome by a method using transduction, transposon (Berg, D. E. and Berg, C. M., Bio/Technol. 1, p. 417, 1983), Mu phage, (Japanese Patent Laid-open Publication (Kokai) No. 2-109985) or homologous recombination (Experiments in Molecular Genetics, Cold Spring Harbor Lab., 1972). Further, the target gene can also be introduced by a method of disrupting a gene using a linear DNA produced by PCR (Kirill A., Datsenko et al., Proc. Natl. Acad. Sci. USA., 97 (12), 6640–6645 (2000)).

Examples of the γ-proteobacteria bred by recombinant DNA techniques as described above include, for example, bacteria belonging to the genus *Escherichia* having enhanced activities of dihydrodipicolinate synthase having a mutation canceling feedback inhibition by L-lysine, aspartokinase, dihydrodipicolinate reductase and so forth, of which feedback inhibition by L-lysine is desensitized, and having L-lysine producing ability (U.S. Pat. No. 6,040,160), and bacterium belonging to the genus *Enterobacter* (the genus *Pantoea*) having enhanced activity of citrate synthase, phosphoenolpyruvate carboxylase or glutamate dehydrogenase and having L-glutamic acid producing ability (EP 0 952 221 A2, EP 0 999 282 A2, EP 1 078 989 A2).

The γ-proteobacterium used for the present invention is a bacterium having an ability to produce the aforementioned target substance and modified so that the ArcA protein does not normally function in a cell. The expression of "modified so that the ArcA protein does not normally function in a cell" means that it is modified so that the function of the ArcA protein should be completely eliminated, or the function should be reduced compared with an unmodified strain of *Escherichia* bacterium such as a wild strain. The state where the ArcA protein does not normally function may be, for example, a state where transcription or translation of the arcA gene is inhibited, and hence the gene product thereof, the ArcA protein, is not produced or the production thereof is reduced, or a state where the produced ArcA protein is mutated, and thus the proper function of the ArcA protein is reduced or eliminated. Examples of the γ-proteobacteria in which the ArcA protein does not normally function include, typically, a gene-disrupted strain in which the arcA gene on the chromosome is disrupted by a genetic recombination technique, and a mutant strain in which an expression regulatory sequence or coding region of the arcA gene on the chromosome is mutated, and therefore functional ArcA protein is no longer produced.

Examples of the ArcA protein contained in a wild strain or unmodified strain used for the breeding of the bacterium of the present invention include, for example, a protein having the amino acid sequence of SEQ ID NO: 32. Further, examples of the arcA gene include, for example, DNA having the nucleotide sequence of SEQ ID NO: 31. Moreover, the gene may have the sequence in which any codon is replaced with another equivalent codon. In the present invention, the term "DNA coding for a protein" means that, when DNA is double-stranded, either one of the strands codes for the protein.

Further, the ArcA protein contained in the wild strain or unmodified strain is not limited to a wild-type protein, and it may contain substitution, deletion, insertion, addition or the like of one or more amino acid residues so long as the protein has the activity of ArcA protein. Although the number of "several" amino acid residues referred to herein differs depending on position or type of amino acid residues in the three-dimensional structure of the protein, it may be specifically 2 to 30, preferably 2 to 20, more preferably 2 to 10.

The aforementioned "activity of the ArcA protein" is an activity that improves the ability to produce a target substance when the protein does not function normally compared with the case where the protein normally functions. In other words, the activity of the ArcA protein means that a γ-proteobacterium modified so that the protein does not normally function produces and accumulates a larger amount of the target substance in a medium compared with an unmodified strain of the γ-proteobacterium such as a wild strain. Examples of wild strain of *E. coli* include, for example, the K12 strain and derivative thereof such as *E. coli* MG1655 strain (ATCC No. 47076) and W3110 strain (ATCC No. 27325). Further, examples of unmodified strain of *Pantoea ananatis* (*Enterobacter agglomerans*) include the strains AJ13355 (FERM BP-6614), AJ13356 (FERM BP-6615) and AJ13601 (FERM BP-7207).

The aforementioned substitution, deletion, insertion, addition, inversion or the like of amino acid residues also include naturally occurring mutations or variations due to difference in individual, species, strain or the like of the microorganism containing the ArcA protein.

Examples of such mutants or variants of the arcA gene as mentioned above include DNA that is hybridizable with a nucleotide sequence comprising the sequence of the nucleotide numbers 101 to 817 in SEQ ID NO: 31 or a probe that can be produced from the nucleotide sequence under the stringent condition and codes for a protein having an activity similar to that of ArcA. The "stringent condition" used herein is a condition under which a so-called specific hybrid is formed, and a non-specific hybrid is not formed. It is difficult to clearly express this condition by using any numerical value. However, for example, the stringent condition is exemplified by a condition under which DNAs having high homology, for example, DNAs having homology of 50% or more, preferably 70% or more, more preferably 80% or more, are hybridized with each other, but DNAs having homology lower than the above are not hybridized with each other. More specifically, the stringent condition is exemplified by a condition under which DNAs are hybridized with each other at a salt concentration corresponding to an ordinary condition of washing in Southern hybridization, i.e., 1×SSC, 0.1% SDS, preferably 0.1×SSC, 0.1% SDS, at 60° C.

As the probe, a partial sequence of the nucleotide sequence of SEQ ID NO: 31 can also be used. Such a probe can be prepared by PCR using oligonucleotides produced based on the nucleotide sequence of SEQ ID NO: 31 as primers and a DNA fragment containing the nucleotide sequence of SEQ ID NO: 31 as a template. When a DNA fragment having a length of about 300 bps is used as the probe, the washing conditions for the hybridization may consist of 50° C., 2×SSC and 0.1% SDS.

The terms arcA gene and ArcA protein used hereafter are not limited to those having the nucleotide sequence or amino acid sequence shown in SEQ ID NO: 31 or 32, but include mutants or homologues thereof. As an example of the homologue, the nucleotide sequence of arcA gene and the amino acid sequence of ArcA of *Pantoea ananatis* are shown in SEQ ID No: 19 and 20.

The bacterium of the present invention is a bacterium modified so that the ArcA protein does not normally function, specifically, a γ-proteobacterium of which arcA gene is disrupted, for example. Such a bacterium can be obtained by, for example, substituting an arcA gene that does not normally function (hereafter also referred to as "disrupted arcA gene") for the arcA gene on the chromosome by homologous recombination utilizing a genetic recombination technique (Experiments in Molecular Genetics, Cold Spring Harbor Laboratory Press (1972); Matsuyama, S. and Mizushima, S., J. Bacteriol., 162, 1196 (1985)).

The mechanism of the homologous recombination is as follows. When a plasmid or the like carrying a sequence exhibiting homology with a chromosomal sequence is introduced into a corresponding bacterial cell, recombination occurs at a site of the homologous sequence at a certain frequency, and thus the introduced plasmid as a whole is integrated into the chromosome. Then, by causing recombination again at the site of the homologous sequence on the chromosome, the plasmid may be removed again from the chromosome. However, depending on the position at which the recombination is caused, the disrupted gene may remain on the chromosome, while the original normal gene may be removed from the chromosome together with the plasmid. By selecting such a bacterial strain, a bacterial strain in which the normal arcA gene is replaced with the disrupted arcA gene can be obtained.

Such a gene disruption technique based on the homologous recombination has already been established, and a method utilizing a linear DNA, a method utilizing temperature sensitive plasmid or the like can be used therefor. The arcA gene can also be disrupted by using a plasmid that contains the arcA gene inserted with a marker gene such as drug resistance gene, and cannot replicate in a target microbial cell. That is, in a transformant that has been transformed with such a plasmid and hence acquired drug resistance, the marker gene is integrated into the chromosome DNA. It is likely that this marker gene has been integrated by homologous recombination of the arcA gene present at the both sides of the marker with these genes on the chromosome, and therefore a gene-disrupted strain can efficiently be selected.

Examples of temperature sensitive plasmid functioning in *Escherichia* bacteria include pMAN997 (International Patent Publication WO99/03988), pHSG415, pHSG422 (Hashimoto-Gotoh, T. et al, Gene, 16, 227–235 (1981)) and so forth.

Specifically, a disrupted arcA gene used for the gene disruption can be obtained by deletion of a certain region of arcA gene by means of digestion with restriction exzyme(s) and religation, by insertion of another DNA fragment (marker gene etc.) into the arcA gene, or by introducing substitution, deletion, insertion, addition or inversion of one or more nucleotides in a nucleotide sequence of coding region of arcA gene, its promoter region or the like by means of site-specific mutagenesis (Kramer, W. and Frits, H. J., Methods in Enzymology, 154, 350 (1987)) or treatment with a chemical reagent such as sodium hyposulfite and hydroxylamine (Shortle, D. and Nathans, D., Proc. Natl. Acad. Sci. U.S.A., 75, 270 (1978)) or the like, so that the activity of the encoded repressor should be reduced or eliminated, or transcription of the arcA gene should be reduced or eliminated. Among these methods, a method utilizing deletion of a certain region of the arcA gene by digestion with a restriction enzyme and religation, or insertion of another DNA fragment into the arcA gene is preferred in view of reliability and stability.

The sequence of arcA gene per se is known, and therefore the arcA gene can be easily obtained by the PCR method or hybridization method based on the sequence. It is sufficient that the arcA gene used for the gene disruption should have homology in such a degree that homologous recombination with the arcA gene contained in the target bacterium should be caused. Specifically, it is sufficient that the homology should be usually 70% or more, preferably 80% or more, more preferably 90% or more.

Disruption of the target gene can be confirmed by analyzing the gene on the chromosome utilizing Southern blotting or PCR method.

Methods for obtaining various genes, hybridization, PCR, preparation of plasmid DNA, digestion and ligation of DNA, transformation etc. used for the present invention are described in Sambrook, J., Fritsch, E. F., Maniatis, T., Molecular Cloning, Cold Spring Harbor Laboratory Press, 1.21 (1989).

Further, a mutant strain in which functional ArcA protein is no longer produced can be obtained by subjecting a γ-proteobacterium to ultraviolet irradiation or treating it with a mutating agent used for usual mutation treatment such as N-methyl-N'-nitrosoguanidine (NTG) or nitrous acid.

By culturing a γ-proteobacterium microorganism having an ability to produce a target substance and modified so that the ArcA protein does not normally function, which can be obtained as described above, in a medium to produce and accumulate the target substance in the medium or cells and collecting the target substance from the medium or cells, the target substance can be produced. According to the present invention, the production efficiency of the target substance can be improved by using a γ-proteobacterium having the aforementioned characteristics. It is estimated that the arcA gene is expressed in a wild strain of γ-proteobacterium concerning the arcA gene during the culture and inhibits the expression of the genes involved in the TCA cycle, whereas in a strain in which the ArcA protein does not normally function, such expression inhibition for the TCA cycle genes is canceled, and thus the above effect should be obtained.

The medium used for the present invention may be an ordinary medium containing a carbon source, nitrogen source, inorganic ions, and other organic components as required. As the carbon source, there can be used saccharides such as glucose, sucrose, lactose, galactose, fructose, arabinose, maltose, xylose, trehalose, ribose and starch hydrolysate, alcohols such as glycerol, mannitol and sorbitol and organic acids such as gluconic acid, fumaric acid, citric acid and succinic acid. As the nitrogen source, there can be used inorganic ammonium salts such as ammonium sulfate, ammonium chloride and ammonium phosphate, organic nitrogen such as soybean protein hydrolysate, ammonia gas, aqueous ammonia and so forth. As organic trace amount nutrients, it is desirable to add required substances, for example, vitamins such as vitamin $B_1$, nucleic acids such as adenine and RNA or yeast extract or the like to the medium in appropriate amounts. Other than the above, potassium phosphate, magnesium sulfate, iron ion, manganese ion and so forth are added in small amounts as required.

The culture may be carried out under conventionally used well-known conditions depending on the bacterial strain used. For example, the culture is preferably carried out under an aerobic condition for 16 to 72 hours. Culture temperature is preferably controlled to be 30° C. to 45° C., and pH is preferably controlled to be 4.5 to 8 during the culture. Inorganic or organic, acidic or alkaline substances as well as ammonia gas and so forth can be used for pH adjustment.

For collection of the target substance from the medium or cells, any special method is not required for the present invention. That is, it can be carried out by a combination of conventionally well-known techniques such as methods utilizing ion exchange resins, precipitation and other techniques depending on the type of the target substance. Further, the target substance accumulated in cells can be collected, after the cells are physically or enzymatically disrupted, from cell extract or membrane fraction depending on the target substance. Furthermore, depending on the target substance, cells containing the target substance can also be used as they are as a microbial catalyst or the like.

EXAMPLES

Hereafter, the present invention will be explained more specifically with reference to the following examples.

Example 1

Disruption of arcA, dam and fnr Genes of *E. coli*

The entire nucleotide sequence of genomic DNA of *E. coli* K-12 strain has been already elucidated (Blattner F. R., Plunkett G., Bloch C. A. et al., Science, 227, 1453–1474 (1997); genetics.wisc.edu). Based on the known nucleotide sequences of arcA, dam and fnr genes, gene-disrupted strains for each of arcA, dam and fnr were produced. In the following procedure, QUAGEN-Genomic-tip System (produced by QIAGEN) was used for the extraction of genomic DNA.

(1) Disruption of arcA Gene of *E. coli*

Primers were synthesized based on the reported nucleotide sequence of arcA, and N- and C-terminal fragments of arcA gene were amplified by PCR method using the genomic DNA of *E. coli* MG1655 strain as a template. Pyrobest DNA Polymerase (produced by Takara Shuzo) was used for PCR, and PCR was performed according to the attached instruction. Primers 1 and 2 were used as the primers for PCR for amplifying N-terminal fragment, and Primers 3 and 4 were used as the primers for PCR for amplifying C-terminal fragment. Primer 1 was designed to contain a HindIII site, and Primer 4 was designed to contain an XbaI site.

Primer 1: cccaagcttaaagcccttacttagctta (sequence complementary to the nucleotide numbers 5482 to 5501 of the nucleotide sequence of GenBank Accession No. AE000510 added with ccc and HindIII site at the 5' end, SEQ ID NO: 1)

Primer 2: tccgcgccatctgtcgcttc (sequence of the nucleotide numbers 4851 to 4870 of the nucleotide sequence of GenBank Accession No. AE000510, SEQ ID NO: 2)

Primer 3: gaagcgacagatggcgcggaaaagctacaagttcaatggt (sequence complementary to the nucleotide numbers 4541 to 4560 of the nucleotide sequence of GenBank Accession No. AE000510 added at the 5' end with a sequence complementary to the nucleotide numbers 4851 to 4870 of the nucleotide sequence of GenBank Accession No. AE000510, SEQ ID NO: 3)

Primer 4: gggtctagaggttgaaaaataaaaacggc (sequence of the nucleotide numbers 4188 to 4207 of the nucleotide sequence of GenBank Accession No. AE000510 added with ggg and XbaI site at the 5' end, SEQ ID NO: 4)

After PCR, the amplified DNA fragments were each purified by using QIAquick PCR Purification Kit (produced by QIAGEN). The purified N-terminal DNA fragment and C-terminal DNA fragment, Primers 1 and 4 were used for the crossover PCR method (A. J. Link, D. Phillips, G. M.

Church, Journal of Bacteriology, 179, 6228–6237 (1997)) to obtain a disrupted arcA fragment. The purified DNA fragment was digested with HindIII and XbaI (produced by Takara Shuzo) and subjected to phenol/chloroform treatment and ethanol precipitation. This fragment was ligated with a temperature sensitive plasmid pMAN997 (International Patent Publication WO99/03988) also digested with HindIII and XbaI by using DNA ligation Kit Ver.2 (produced by Takara Shuzo). JM109 competent cells (produced by Takara Shuzo) were transformed with this ligation solution and applied to an LB agar plate containing 25 µg/mL of ampicillin (produced by Sigma) (LB+ampicillin plate). After the cells were cultured at 30° C. for one day, the grown colonies were cultured in test tubes at 30° C. in LB medium containing 25 µg/mL of ampicillin, and plasmids were extracted by using an automatic plasmid extractor PI-50 (produced by Kurabo Industries). The obtained plasmids were digested with HindIII and XbaI and subjected to agarose gel electrophoresis, and the plasmid inserted with the target fragment was designated as plasmid pMAN_ΔarcA for arcA disruption. The aforementioned pMAN997 is a plasmid obtained by exchanging VspI-HindIII fragments of pMAN031 (S. Matsuyama and S. Mizushima, J. Bacteriol., 162, 1196 (1985)) and pUC19 (produced by Takara Shuzo).

The *E. coli* WC196 strain was transformed with the plasmid pMAN_ΔarcA according to the method of C. T. Chung et al., and colonies were selected on an LB+ampicillin plate at 30° C. The selected clones were cultured overnight at 30° C. as liquid culture, then the culture broth was diluted to $10^{-3}$ concentration and plated on an LB+ampicillin plate, and colonies were selected at 42° C. The selected clones were applied to an LB+ampicillin plate and cultured at 30° C., and then ⅛ of the cells on the plate were suspended in 2 mL of LB medium and cultured at 42° C. for 4 to 5 hours with shaking. The culture broth was diluted to $10^{-5}$ concentration and applied to an LB plate, and several hundreds of colonies among the obtained colonies were inoculated on an LB plate and LB+ampicillin plate to confirm growth and thereby select ampicillin sensitive strains. Colony PCR was performed for several ampicillin sensitive strains to confirm the deletion of arcA gene. In this way, an arcA disrupted-strain derived from *E. coli* WC196, WC196ΔarcA, was obtained.

(2) Disruption of dam Gene of *E. coli*

A dam gene-disrupted strain was produced from WC196 in the same manner as in (1).

Primers were synthesized based on the reported nucleotide sequence of the dam gene, and N- and C-terminal fragments of the dam gene were amplified by PCR method using the genomic DNA of *E. coli* MG1655 strain as a template. Primers 5 and 6 were used as the primers for PCR for amplifying N-terminal fragment, and Primers 7 and 8 were used as the primers for PCR for amplifying C-terminal fragment. Primer 5 was designed to contain a HindIII site, and Primer 8 was designed to contain an XbaI site.

Primer 5: cccaagcttccgtggtatgtcctggtttc (sequence complementary to the nucleotide numbers 5150 to 5169 of the nucleotide sequence of GenBank Accession No. AE000414 added with ccc and HindIII site at the 5' end, SEQ ID NO: 5)

Primer 6: agactgatcaggtcgctatt (sequence of the nucleotide numbers 4741 to 4760 of the nucleotide sequence of GenBank Accession No. AE000414, SEQ ID NO: 6)

Primer 7: aatagcgacctgatcagtctgccttatgcaccgctgtctg (sequence complementary to the nucleotide numbers 4361 to 4380 of the nucleotide sequence of GenBank Accession No. AE000414 added at the 5' end with a sequence complementary to the nucleotide numbers 4741 to 4760 of the nucleotide sequence of GenBank Accession No. AE000414, SEQ ID NO: 7) Primer 8: gggtctagacgtcagattgggaacatagt (sequence of the nucleotide numbers 3931 to 3950 of the nucleotide sequence of GenBank Accession No. AE000414 added with ggg and XbaI site at the 5' end, SEQ ID NO: 8)

After PCR, the amplified DNA fragments were each purified by using QIAquick PCR Purification Kit (produced by QIAGEN). The purified N-terminal DNA fragment and C-terminal DNA fragment, Primers 5 and 8 were used for the crossover PCR method to obtain a deficient type dam fragment. The following procedure was performed in the same manner as in (1) to obtain a dam disrupted-strain WC196Δdam.

(3) Disruption of fnr Gene of *E. coli*

A fnr gene-disrupted strain was produced from WC196 in the same manner as in (1).

Primers were synthesized based on the reported nucleotide sequence of the fnr gene, and N- and C-terminal fragments of the fnr gene were amplified by PCR method using the genomic DNA of *E. coli* MG1655 strain as a template.

Primers 9 and 10 were used as the primers for PCR for amplifying N-terminal fragment, and Primers 11 and 12 were used as the primers for PCR for amplifying C-terminal fragment. Primer 9 was designed to contain a HindIII site, and Primer 12 was designed to contain an XbaI site. A fnr-disrupted strain was produced from WC196 in the same manner as in (1).

Primer 9: cccaagcttgcaattgggccgtcctggcg (sequence complementary to the nucleotide numbers 7981 to 8000 of the nucleotide sequence of GenBank Accession No. AE000231 added with ccc and HindIII site at the 5' end, SEQ ID NO: 9)

Primer 10: tcaagctgatcaagctcatg (sequence of the nucleotide numbers 7501 to 7520 of the nucleotide sequence of GenBank Accession No. AE000231, SEQ ID NO: 10)

Primer 11: caggagttgatcagcttgagaaaaaatgccgaggaacgtc (sequence complementary to the nucleotide numbers 7121 to 7140 of the nucleotide sequence of GenBank Accession No. AE000231 added at the 5' end with a sequence complementary to the nucleotide numbers 7501 to 7520 of the nucleotide sequence of GenBank Accession No. AE000231, SEQ ID NO: 11) Primer 12: gggtctagattggtcgtcctggttaggat (sequence of the nucleotide numbers 6671 to 6690 of the nucleotide sequence of GenBank Accession No. AE000231 added with ggg and XbaI site at the 5' end, SEQ ID NO: 12)

After PCR, the amplified DNA fragments were each purified by using QIAquick PCR Purification Kit (produced by QIAGEN). The purified N-terminal DNA fragment and C-terminal DNA fragment, Primers 9 and 12 were used for the crossover PCR method to obtain a deficient type dam fragment. The following procedure was performed in the same manner as in (1) to obtain a fnr disrupted-strain WC196Δfnr.

Example 2

Effect of arcA Disruption on L-lysine Production in E. coli Strain

The arcA gene-disrupted strain, WC196ΔarcA strain, the dam gene-disrupted strain, WC196Δdam, the fnr gene-disrupted strain, WC196Δfnr, and the parent strain thereof, WC196, were cultured, and their L-lysine production amounts were measured. The media, culture methods and analysis method for the measurement are shown below.

[Base Medium: E-100 Medium]

|  | Final concentration |
| --- | --- |
| Glucose | 10 g/L (separately sterilized) |
| NH₄Cl | 20 mM |
| NaHPO₄ | 40 mM |
| KH₂PO₄ | 30 mM |
| CaCl₂ | 0.01 mM |
| FeSO₄ | 0.01 mM |
| MnSO₄ | 0.01 mM |
| citric acid | 5 mM |
| thiamine hydrochloride | 2 mM (separately sterilized) |
| casamino acid | 2.5 g/L (separately sterilized) |
| MES-NaOH (pH 6.8) | 50 mM (separately sterilized) |

[Culture Method]

Refresh Culture:

Stock bacteria were inoculated.

LB agar medium (drug was added as required), 37° C., 24 hours.

Seed Culture:

The bacteria undergone the refresh culture were inoculated in a volume of 2 mL to LB medium.

LB medium (drug was added as required), 37° C., overnight.

Main Culture:

1/16 of the bacteria on the seed culture cell plate were inoculated.

E-100 medium (drug was added as required), 37° C., 20 ml in 500 ml-volume Sakaguchi flask.

[Analysis Method]

The culture broth was sampled in a volume of 500 μl in a time course, and glucose concentration and L-lysine accumulation in the culture broth were measured. The glucose concentration and L-lysine accumulation were measured for supernatant of the culture broth obtained after centrifugation at 15,000 rpm for 5 minutes diluted to an appropriate concentration with water by using Biotech Analyzer (Sakura Seiki). The results are shown in FIG. 1.

As a result, it was observed that the fnr gene-disrupted strain exhibited L-lysine accumulation equivalent to that of the control strain, and the dam gene-disrupted strain exhibited reduced accumulation compared with the control strain. On the other hand, it was recognized that the L-lysine accumulation of the arcA gene-disrupted strain was improved compared with the control strain.

Example 3

Effect of arcA Disruption on L-glutamic Acid Production in E. coli Strain

Since L-lysine accumulation improvement effect was observed in Example 2 by the use of arcA gene disruption, effect of the arcA gene on the L-glutamic acid fermentation was examined in this example.

In order to confirm effect of deficiency of the arcA gene on L-glutamic acid production in E. coli MG1655, E. coli MG1655-derived sucA deficient strain (MG1655ΔsucA) and E. coli MG1655-derived sucA and arcA doubly deficient strain (MG1655ΔsucAΔarcA) were constructed.

(1) Disruption of sucA Gene of E. coli

A sucA gene-disrupted strain was produced from MG1655 in the same manner as in Example 1.

Primers were synthesized based on the reported nucleotide sequence of the sucA gene, and N- and C-terminal fragments of the sucA gene were amplified by PCR method using the genomic DNA of E. coli MG1655 strain as a template.

Primers 13 and 14 were used as the primers for PCR for amplifying N-terminal fragment, and Primers 15 and 16 were used as the primers for PCR for amplifying C-terminal fragment. Primer 13 was designed to contain a HindIII site, and Primer 16 was designed to contain an XbaI site. A sucA-disrupted strain was produced from MG1655 in the same manner as in (1).

Primer 13: cccaagcttctgcccctgacactaagaca (sequence of the nucleotide numbers 10721 to 10740 of the nucleotide sequence of GenBank Accession No. AE000175 added with ccc and HindIII site at the 5' end, SEQ ID NO: 13)

Primer 14: cgaggtaacgttcaagacct (sequence complementary to the nucleotide numbers 11501 to 11520 of the nucleotide sequence of GenBank Accession No. AE000175, SEQ ID NO: 14)

Primer 15: aggtcttgaacgttacctcgatccataacgggcagggcgc (sequence of the nucleotide numbers 12801 to 12820 of the nucleotide sequence of GenBank Accession No. AE000175 added at the 5' end with a sequence of the nucleotide numbers 10501 to 11520 of the nucleotide sequence of GenBank Accession No. AE000175, SEQ ID NO: 15)

Primer 16: gggtctagaccactttgtcagtttcgatt (sequence complementary to the nucleotide numbers 13801 to 13820 of the nucleotide sequence of GenBank Accession No. AE000175 added with ggg and XbaI site at the 5' end, SEQ ID NO: 16)

After PCR, the amplified DNA fragments were each purified by using QIAquick PCR Purification Kit (produced by QIAGEN). The purified N-terminal DNA fragment and C-terminal DNA fragment, Primers 13 and 16 were used for the crossover PCR method to obtain a deficient type sucA fragment. The following procedure was performed in the same manner as in (1) to obtain a sucA disrupted-strain, MG1655ΔsucA.

(2) Preparation of sucA and arcA Gene Doubly Deficient Strain of E. coli

In the same manner as in Example 1, the arcA gene of MG1655ΔsucA was disrupted to prepare a sucA and arcA doubly deficient strain (MG1655ΔsucAΔarcA).

Similarly, sucA and dam doubly deficient strain (MG1655ΔsucAΔdam) and sucA and fnr doubly deficient strain (MG1655ΔsucAΔfnr) were produced.

In order to examine effect of arcA gene disruption on L-glutamic acid fermentation, the doubly deficient strains for the genes, MG1655ΔsucAΔarcA, MG1655ΔsucAΔdam, and MG1655ΔsucAΔfnr strains as well as the sucA gene deficient strain, MG1655ΔsucA, as a control were cultured, and L-glutamic acid production amounts were measured. The media, culture methods and analysis method for the measurement are shown below.

[Base Medium: MS Medium]

|  | Final concentration |
| --- | --- |
| Glucose | 40 g/L (separately sterilized) |
| MgSO$_4$.7H$_2$O | 1 g/L (separately sterilized) |
| (NH$_4$)$_2$SO$_4$ | 16 g/L |
| KH$_2$PO$_4$ | 1 g/L |
| Yeast extract | 2 g/L |
| FeSO$_4$ | 0.01 g/L |
| MnSO$_4$ | 0.01 g/L |
| CaCO$_3$ | 30 g/L (separately sterilized) |

[Culture Methods]

Refresh Culture:

Stock bacteria were inoculated.

LB agar medium (drug was added as required), 37° C., 24 hours.

Seed Culture in Test Tube:

The bacteria undergone the refresh culture were inoculated.

LB liquid medium (drug was added as required), 37° C., 16 hours.

Main Culture:

10% of the liquid medium for the seed culture was inoculated.

MS liquid medium (drug was added as required), 37° C., 20 ml in 500 ml-volume Sakaguchi flask.

[Analysis Method]

The culture broth was sampled in a volume of 500 μl in a time course, and glucose concentration and L-glutamic acid accumulation in the culture broth were measured. The glucose concentration and L-glutamic acid concentration were measured for supernatant of the culture broth obtained after centrifugation at 15,000 rpm for 5 minutes diluted to an appropriate concentration with water by using Biotech Analyzer (Sakura Seiki). The L-glutamic acid accumulation and yield at the point where the saccharide was depleted are shown in Table 1.

TABLE 1

L-glutamic acid accumulation and yield of sucA and arcA-disrupted strain

| Strain | L-glutamic acid accumulation (g/L) | L-glutamic acid yield (%) |
| --- | --- | --- |
| MG1655ΔsucA | 15.4 | 36.9 |
| MG1655ΔsucAΔarcA | 17.0 | 41.7 |
| MG1655ΔsucAΔdam | 14.2 | 35.5 |
| MG1655ΔsucAΔfnr | 14.6 | 36.6 |

As a result, both of the accumulation and yield of glutamic acid were slightly lower in the sucA and dam gene-disrupted strain compared with the control, and they were comparable to those of the control in the sucA and fnr gene-disrupted strain. On the other hand, it was recognized that both of the accumulation and yield of L-glutamic acid were improved in the sucA and arcA gene-disrupted strain compared with the control strain.

Example 4

Disruption of arcA Gene of *Pantoea ananatis*

<1> Acquisition of arcA Gene of *Pantoea ananatis*

(1) Construction of *Pantoea ananatis* Producing L-glutamic Acid Under a Low pH Condition ArcA is a global regulator universally existing in *E. coli* and other relative species. Using a bacterium belonging to the genus *Pantoea, Pantoea ananatis* AJ13601, which is a relative to *E. coli*, arcA gene of *Pantoea ananatis* was obtained based on a known nucleotide sequence of *E. coli* arcA. The strain AJ13601 was obtained as follows (refer to EP 1 078 989 A2). The strain AJ13355 was isolated from soil in Iwata-shi, Shizuoka, Japan as a strain which can graw under a low pH in a medium containing L-glutamic acid and carbon source. From the strain AJ13355, the strain SC17 was selected as a less mucus producing mutant which shows good growth. The strain SC17sucA, in which α-ketoglutarate dehydrogenase (□KGDH) gene is disrupted, was constructed from the strain SC17. To the strain SC17sucA, the plasmid pSTVCB containing a citrate synthase gene (gltA) derived from *Brevibacterium lactofermentum* (pSTVCB), and the plasmid RSFCPG containing gltA, phosphoenolpyruvate carboxylase gene (ppc) and glutamate dehydrogenase gene (gdhA) derived from *E. coli* were introduced. From the obtained transformants, the strain AJ13601 was selected as a strain which has an increased resistance to high concentration of L-glutamic acid under a low pH condition. The strain AJ13601 has been deposited at National Institute of Bioscience and Human-Technology, Agency of Industrial Science and Technology (presently, the independent administrative corporation, International Patent Organism Depositary, National Institute of Advanced Industrial Science and Technology, Chuo Dai-6, 1-1 Higashi 1-Chome, Tsukuba-shi, Ibaraki-ken, Japan, postal code: 305-5466) on Aug. 18, 1999, under accession number of FERM P-17516, and then, the deposit was converted into international deposit under the provisions of the Budapest Treaty on Jul. 6, 2000 and received accession number of FERM BP-7207 (refer to EP 1 078 989 A2).

(2) Acquisition of arcA Gene of *Pantoea ananatis* AJ13601

Genomic DNA of *Pantoea ananatis* AJ13601 was extracted using QIAGEN-Genomic-tip System (produced by QIAGEN). By PCR using the genomic DNA as a template and the following oligonucleotides as primers, 759 bp DNA fragment containing arcA gene ORF was obtained. Pyrobest DNA Polymerase (produced by Takara Shuzo) was used for PCR, and PCR was performed according to the attached instruction. Primers 17 and 18 were used as PCR primers for amplification. Primer 17 was designed to contain a EcoRI site, and Primer 18 was designed to contain an SphI site, respectively.

Primer 17: cccgaattccctgtttcgatttagttggc (sequence complementary to the nucleotide numbers 4980–4999 of the nucleotide sequence of GenBank Accession No. AE000510 added with EcoRI site at the 5' terminus: SEQ ID NO: 17)

Primer 18: cccgcatgcgattaatcttccagatcacc (sequence of the nucleotide numbers 4245–4264 of GenBank Accession No. AE000510 added with SphI site at the 5' terminus: SEQ ID NO: 18)

The obtained DNA fragment was inserted to the cloning vector pSTV29 (produced by Takara Shuzo) in the forward direction as to the direction of transcription by lacZ gene utilizing EcoRI and SphI sites designed in the primers to obtain pSTV29_EaarcA. The nucleotide sequence of the cloned sequence is shown in SEQ ID No: 19. The deduced amino acid sequence encoded by the ORF is shown in SEQ ID No: 20. The obtained ORF shows about 81.2% identity in the nucleotide sequence and about 92.1% in the amino acid sequence to the arcA gene of E. coli. Thus the ORF is considered to encode ArcA of Pantoea ananatis.

<2> Disrution of arcA Gene of Pantoea ananatis

Pantoea ananatis strain G106S was used for construction of arcA gene-disrupted strain of Pantoea ananatis. Among the two plasmids, RSFCPG and pSTVCB, harbored by the strain AJ13601, the strain G106S harbors RSFCPG alone and is deleted pSTVCB. The arcA gene-disrupted strain was constructed from the strain G106S. Then pSTVCB was introduced to the obtained gene-disrupted strain to obtain the arcA gene-disrupted strain of AJ13601. The procedure will be explained below in detail.

(1) Constructin of a Plasmid for Conjugative Transfer for Disruption of arcA Gene Utilization of conventional breeding by recombination on choromosome with a temperature-sensitive plasmid is not simple in a recombination procedure for Pantoea ananatis because of characteristics of Pantoea ananatis that it can hardly grow at 42° C. Therefore, a technique of recombination on a choromosome utilizing conjugative transfer was used in this experiment. For the conjugative transfer method, it is necessary to construct a plasmid which does not contain a replication origin (ori) of Pantoea ananatis, that is, a plasmid which cannot replicate Pantoea ananatis. Thus, the oriR6K and mobRP4 region was amplified by PCR using primers 21 and 22, and a plasmid for Tn5 transfer, pUT/miniTn5-Cm (Lorenzo V., et al., Journal of Bacteriology, 172, 6568-(1990); Herrero M., et al., Journal of Bacteriology, 172, 6557 (1990)) as a template. Besides, a fragment containing multi-cloning site and chloramphenicol resistance gene was amplified by PCR using primers 23 and 24, and pHSG399 as a template. Each of the obtained amilified fragment was digested with BglII (produced by Takara Shuzo) and the fragments were ligated with DNA ligation Kit ver.2 (produced by Takara Shuzo).

Then, E. coli strain S17-1 λpir (R. Simon., et al., BIO/TECHNOLOGY NOVEMBER 1983, 784–791 (1983)) was transformed with the ligation mixture, and applied onto LB agar plate containing 30 µg/ml of chloramphenicol. After culture for one day at 37° C., appeared colonies were cultured in LB medium containing 30 µg/ml of chloramphenicol in test tubes at 37° C. Plasmids were obtained from each of the culture using QIAprep Mini Spin column Kit (produced by QIAGEN). Obtained plasmids were digested with BglII, and a plasmid which has a unique BglII recognition site was designated as the plasmid for conjugative transfer, pUT399 Cm.

Primer 21:
tcatagatcttttagattgatttatggtgc  (SEQ ID NO: 21)

Primer 22:
ccacagatctaattcccatgtcagccgtta  (SEQ ID NO: 22)

Primer 23:
ataaagatctgtgtccctgttgataccggg  (SEQ ID NO: 23)

Primer 24:
ggggagatcttgcaaggcgattaagttggg  (SEQ ID NO: 24)

Then, a kanamycin resistance gene was introduced into pUT399 Cm and deleted the chloramphenicol resistance gene from the plasmid according to the following procedure. The kanamycin resistance gene was amplified by PCR using primers 25 and 26, and pMW 219 (produced by Nippon Gene) as a template. Pyrobest DNA Polymerase (produced by Takara Shuzo) was used for PCR, and PCR was performed according to the attached instruction. Each of primers 25 and 26 was added with BglII site at the 5' terminus. Obtained DNA fragment and pUT399 were digested with BglII (produced by Takara Shuzo), and ligated with DNA ligation Kit ver.2 (produced by Takara Shuzo). Then, E. coli strain S17-1 λpir (R. Simon., et al., BIO/TECHNOLOGY NOVEMBER 1983, 784–791 (1983)) was transformed with the ligation mixture, and applied onto LB agar plate containing 25 µg/ml of kanamycin (LB+kanamycin plate). After culture for one day at 37° C., appeared colonies were cultured in LB medium containing 25 µg/ml of kanamycin in test tubes at 37° C. Plasmids were obtained from each of the culture using QIAprep Spin Miniprep Kit (produced by QIAGEN). Obtained plasmids were digested with BglII, and subjected to agarose gel electrophoresis, and the plasmid inserted with the target fragment was designated as plasmid pUT399 CmKm.

Primer 25:
cccagatctagttttcgccccgaagaacg  (SEQ ID NO: 25)

Primer 26:
cccagatctccagagtcccgctcagaaga  (SEQ ID NO: 26)

Then, the chloramphenicol resistance gene was deleted from pUT399 CmKm as described below. pUT399 CmKm was digested with HindIII (produced by Takara Shuzo) and was ligated with DNA ligation Kit ver.2 (produced by Takara Shuzo). E. coli strain S17-1 λpir (R. Simon., et al., BIO/TECHNOLOGY NOVEMBER 1983, 784–791 (1983)) was transformed with the ligation mixture, and applied onto LB agar plate containing 25 µg/ml of kanamycin (LB+kanamycin plate). After culture for one day at 37° C., appeared colonies were cultured on LB agar plate containing 25 µg/ml of kanamycin and LB agar plate containing 30 µg/ml of chloramphenicol (produced by Sigma) at 37° C. and a strain showing chloramphenicol sensitivity. The strain was cultured in LB medium containing 25 µg/ml of kanamycin for one day at 37° C. and plasmid was obtained from the culture using QIAprep Spin Miniprep column Kit (produced by QIAGEN). Obtained plasmids was designated pUT399 km.

Primers were prepared based on the nucleotide sequence of arcA gene obtained in the above <1>, and N-terminal fragment and C-terminal fragment of the arcA gene were amplified using the primers and pSTV29_EaarcA as a template. Pyrobest DNA Polymerase (produced by Takara Shuzo) was used for PCR, and PCR was performed according to the attached instruction. Primers 27 and 28 were used as the primers for PCR for amplifying N-terminal fragment, and Primers 29 and 30 were used as terminal fragment, and Primers 29 and 30 were used as the primers for PCR for amplifying C-terminal fragment. Primer 27 was designed to contain an EcoRI site, and Primer 30 was designed to contain an SphI site, respectively.

```
Primer 27:                                    (SEQ ID
cccgaattcgcgaccgatggtgcagagat                 NO: 27)

Primer 28:                                    (SEQ ID
aaggcaaattcatggtgcgc                          NO: 28)

Primer 29:                                    (SEQ ID
gcgcaccatgaatttgccttacccaatgaagagcgtcgcc      NO: 29)

Primer 30:                                    (SEQ ID
cccgcatgcaccttcgccgtgaatggtgg                 NO: 30)
```

After PCR, the amplified DNA fragments were each purified by using QIAquick PCR Purification Kit (produced by QIAGEN). The purified N-terminal DNA fragment and C-terminal DNA fragment, Primers 27 and 30 were used for the crossover PCR method (A. J. Link, D. Phillips, G. M. Church, Journal of Bacteriology, 179, 6228–6237 (1997)) to obtain a disrupted arcA fragment.

The purified DNA fragment was digested with EcoRI and SphI (produced by Takara Shuzo) and subjected to phenol/chloroform treatment and ethanol precipitation. This fragment was ligated with a plasmid pUT399 Km also digested with EcoRI and SphI by using DNA ligation Kit Ver.2 (produced by Takara Shuzo). E. coli strain S17-1 λpir (R. Simon., et al., BIO/TECHNOLOGY NOVEMBER 1983, 784–791 (1983)) was transformed with the ligation 25 μg/ml of kanamycin. After culture for one day at 37° C., appeared colonies were cultured in LB medium containing 25 μg/ml of kanamycin in test tubes at 37° C. Plasmid was obtained from the culture using QIAprep Spin Miniprep column Kit (produced by QIAGEN). Obtained plasmids were digested with EcoRI and SphI, and subjected to agarose gel electrophoresis. The plasmid inserted with the target fragment was designated as plasmid pUT399 Km_ΔarcA for arcA disruption.

(2) Disrution of arcA Gene of *Pantoea ananatis* by Conjugative Transfer

Gene disruption using homologous recombination method with the above-mentioned pUT399 Km_ΔarcA. The strain G106S was used as a plasmid donor strain. Screening was performed with a medium comprising 5 g/L of glucose (produced by Junsei Kagaku), 5 g/L of Yeast Extract (produced by Difco), 10 g/L of Trypotone-Peptone (Difco), 10 g/L of NaCl (Junsei Kagaku), 6 g/L of $Na_2HPO_4$, 3 g/L of $KH_2PO_4$, 1 g/L of $NH_4Cl$, and 1.5 g/L of $CaCl_2.2H_2O$ (hereinafter referred to as "LBG-M9 medium") added with containing 25 μg/mL of tetracycline, 25 μg/ml of kanamycin and agar (hereinafter referred to as "LBG-M9+Tet+Km" plate). On the agar medium, the strain G106S into which pUT399 Km_ΔarcA has been incorporated on its chromosome can be selected as a single-recombination strain, that is, arcA gene-disrupted strain, since the plasmid derived from pUT399 cannot replicate in *Pantoea ananatis* as described above. E. coli strain S17-1 λpir (R. Simon., et al., BIO/TECHNOLOGY NOVEMBER 1983, 784–791 (1983)) was transformed with pUT399 Km_ΔarcA, and applied onto LB agar plate containing 25 μg/ml of kanamycin. After culture, obtained transformant, E. coli S17-1 λpir/pUT399 Km_ΔarcA, was cultured in LBG-M9 medium containing 25 μg/ml of tetracycline for one day at 37° C. Besides, the strain G106S were cultured in LBG-M9 medium containing 25 μg/ml of tetracycline for one day at 34° C. The each of culture media was centrifuged and obtained cells were suspended in 50 μl of LB medium, respectively. 25 μl of each suspension was mixed and cultured in LBG-M9 agar medium for one hour at a room temperature. Subsequently, the culture was continued for 3 hours at 34° C. to cause conjugative transfer. Then the cultured cells diluted to $10^{-1}$, $10^{-2}$ or $10^{-3}$ concentration were applied to LBG-M9+Tet+Km plate and strains resistant to tetracycline and kanamycin were selected. Colony PCR was performed for some strains among the selected strains to confirm deletion of arcA gene. Thus, the arcA-disrupted strain derived from G106S, G106SΔarcA was obtained.

(3) Introduction of pSTVCB into G106SΔarcA and Production of L-glutamic Acid

The strain G106SΔarcA was transformed with pSTVCB. Obtained transformant G106SΔarcA/pSTVCB is equivalent to arcA gene-disrupted strain of the above-mentioned AJ13601 (AJ13601ΔarcA). The strain G106SΔarcA/pSTVCB and the strain AJ13601 as a control were cultured, and their L-glutamic acid production amounts were measured, respectively. The media, culture methods and analysis method for the measurement are shown below.

[Evaluation Medium for L-glutamic Acid]

|  | Final concentration |
|---|---|
| Sucrose | 30 g/L (separately sterilized) |
| $MgSO_4.7H_2O$ | 0.5 g/L (separately sterilized) |
| $(NH_4)_2SO_4$ | 20 g/L |
| $KH_2PO_4$ | 2 g/L |
| Yeast extract | 2 g/L |
| $FeSO_4$ | 0.02 g/L |
| $MnSO_4$ | 0.02 g/L |
| Lysine | 0.2 g/L |
| Methionine | 0.2 g/L |
| Diamino pimelate | 0.2 g/L |
| pH7.0 (KOH) |  |
| $CaCO_3$ | 20 g/L (separately sterilized) |

[Culture Methods]

Seed Culture in Test Tube:

Stock bacteria were inoculated.

LBG-M9 agar medium (drug was added as required), 34° C., 24 hours.

Main Culture:

Three platinum loops of the seed culture was inoculated.

Base medium (drug was added as required), 34° C., 24 hours.

5 ml per test tube.

[Analysis Method]

The culture broth was sampled in a volume of 400 μl in a time course, and sucrose concentration and L-glutamic acid accumulation in the culture broth were measured. The sucrose concentration and L-glutamic acid concentration were measured for supernatant of the culture broth obtained after centrifugation at 15,000 rpm for 5 minutes diluted to an appropriate concentration with water by using Biotech Analyzer (Sakura Seiki). The L-glutamic acid accumulation and yield at the point where the saccharide was depleted are shown in Table 2.

TABLE 2

L-glutamic acid accumulation and yield of arcA-disrupted strain

| Strain | L-glutamic acid accumulation (g/L) | L-glutamic acid yield (%) |
| --- | --- | --- |
| G106(AJ13601) | 16.3 | 50.8 |
| G106ΔarcA(AJ13601ΔarcA) | 17.4 | 54.3 |

As a result, it was recognized that both of the accumulation and yield of L-glutamic acid were improved in the arcA gene-disrupted strain compared with the control strain.

Example 5

Effect of arcA Disruption on L-arginine Production in *E. coli* Strain

In the above Example 2, it was recognized that both of the accumulation and yield of L-glutamic acid were improved in the sucA and arcA gene-disrupted strain compared with the control strain, sucA-disrupted strain.

Then, the effect on the production of L-arginine which is produced using glutamic acid as a substrate. *E. coli* strain 237 was used as an L-arginine producing strain. The strain 237 was deposited at Russian National Collection of Industrial Microorganisms (VKPM) on Apr. 10, 2000, under accession number of VKPM B-7925, and then, the deposit was converted into international deposit under the provisions of the Budapest Treaty on May 18, 2001.

(1) Construction of arcA Gene-disrupted Strain of *E. coli* Strain 237

An arcA gene of the strain 237 was disrupted to prepare an arcA gene-disrupted strain, 237ΔarcA in the same manner as in Example 1.

(2) Production of L-arginine

To evalutate an effect of arcA gene disruption on L-aniginine fermentation, arcA gene-disrupted strain of 237, 237ΔarcA, and the strain 237 as a control were cultured and their L-arginine production amounts were measured. The media, culture methods and analysis method for the measurement are shown below.

[Evaluation Medium for L-arginine]

| | Final concentration |
| --- | --- |
| Glucose | 60 g/L (separately sterilized) |
| $MgSO_4 \cdot 7H_2O$ | 1 g/L (separately sterilized) |
| $(NH_4)_2SO_4$ | 25 g/L |
| $KH_2PO_4$ | 2 g/L |
| Yeast extract | 5 g/L |
| Thiamine | 0.1 mg/L |
| pH7.2 | |
| $CaCO_3$ | 25 g/L (separately sterilized) |

[Culture Methods]

Seed Culture in Test Tube:
  Stock bacteria were inoculated.
  LB agar medium (drug was added as required), 32° C., 24 hours.

Main Culture:
  One platinum loops of the seed culture was inoculated.
  Evaluation medium for arginine (drug was added as required), 32° C., 3 days.
  2 ml per test tube.

[Analysis Method]

The culture broth was sampled in a volume of 500 μl in a time course, and glucose concentration and L-arginine accumulation in the culture broth were measured. The glucose concentration and the L-arginine concentration were measured for supernatant of the culture broth obtained after centrifugation at 15,000 rpm for 5 minutes diluted to an appropriate concentration with water by using Biotech Analyzer (Sakura Seiki) and Amino Acids Analyser L-8500 (HITACHI Keisokuki service). The L-arginine accumulation and yield at the point where the saccharide was depleted are shown in Table 3.

TABLE 3

L-arginine accumulation and yield of arcA-disrupted strain

| Strain | L-arginine accumulation (g/L) | L-arginine yield (%) |
| --- | --- | --- |
| 237 | 4.04 | 6.73 |
| 237ΔarcA | 14.8 | 24.7 |

It was recognized that both of the accumulation and yield of L-arginine were improved in the arcA gene-disrupted strain compared with the control strain.

---

What is claimed is:

1. A method for producing a target substance synthesized via the tricarboxylic acid cycle comprising:
   (a) culturing a γ-proteobacterium wherein production of ArcA protein is reduced or eliminated, and wherein said γ-proteobacterium has an improved ability to produce a target substance synthesized via the tricarboxylic acid cycle as compared to a wild-type γ-proteobacterium in a medium; and
   (b) collecting said target substance from the culture.

2. The method according to claim 1, wherein said ArcA protein is selected from the group consisting of:
   (A) a protein comprising the amino acid sequence of SEQ ID NO: 32; and
   (B) a protein comprising up to 10 amino acid substitutions, deletions, or insertions in the amino acid sequence of SEQ ID NO: 32.

3. The method according to claim 1, wherein said ArcA protein is selected from the group consisting of:
   (A) a protein comprising the amino acid sequence of SEQ ID NO: 32; and
   (B) a protein comprising an amino acid sequence which is at least 70% homologous to SEQ ID NO: 32.

4. The method according to claim 1, wherein said production of the ArcA protein is reduced or eliminated by disruption of an arcA gene on a chromosome.

5. The method according to claim 4, wherein said arcA gene is selected from the group consisting of:
   (a) DNA containing the nucleotide sequence of the nucleotide number 101 to 817 of SEQ ID NO: 31; and
   (b) DNA which is able to hybridize with the nucleotide sequence of the nucleotide numbers 101 to 817 of SEQ ID NO: 31 under stringent conditions comprising wash ing at a salt concentration of 1×SSC, 0.1% SDS at 65° C.

6. The method according to claim 1, comprising a bacterium belonging to the genus *Escherichia*.

7. The method according to claim 1, wherein said target substance comprises an L-amino acid.

8. The method according to claim 7, wherein said L-amino acid is selected from the group consisting of L-lysine, L-glutamic acid, L-arginine, and L-threonine.

* * * * *

SEQUENCE LISTING

<160> NUMBER OF SEQ ID NOS: 32

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: primer for
      amplifying Escherichia coli arcA gene

<400> SEQUENCE: 1

```
cccaagctta aagcccttta cttagctta                                          29
```

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: primer for
      amplifying Escherichia coli arcA gene

<400> SEQUENCE: 2

```
tccgcgccat ctgtcgcttc                                                    20
```

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: primer for
      sequencing of Escherichia coli arcA gene

<400> SEQUENCE: 3

```
gaagcgacag atggcgcgga aaagctacaa gttcaatggt                              40
```

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: primer for
      sequencing of Escherichia coli arcA gene

<400> SEQUENCE: 4

```
gggtctagag gttgaaaaat aaaaacggc                                          29
```

<210> SEQ ID NO 5
<211> LENGTH: 29
<212> TYPE: DNA
<213> ORGANISM: Artificial Sequence
<220> FEATURE:
<223> OTHER INFORMATION: Description of Artificial Sequence: primer for
      amplifying Escherichia coli dam gene

<400> SEQUENCE: 5

```
cccaagcttc cgtggtatgt cctggtttc                                          29
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: primer for
      amplifying Escherichia coli dam gene

<400> SEQUENCE: 6

```
agactgatca ggtcgctatt                                                    20
```

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: primer for
      sequencing of Escherichia coli dam gene

<400> SEQUENCE: 7

```
aatagcgacc tgatcagtct gccttatgca ccgctgtctg                              40
```

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: primer for
      amplifying Escherichia coli dam gene

<400> SEQUENCE: 8
gggtctagac gtcagattgg gaacatagt                                      29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: primer for
      amplifying Escherichia coli fnr gene

<400> SEQUENCE: 9
cccaagcttg caattgggcc gtcctggcg                                      29

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: primer for
      amplifying Escherichia coli fnr gene

<400> SEQUENCE: 10
tcaagctgat caagctcatg                                                20

<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: primer for
      amplifying Escherichia coli fnr gene

<400> SEQUENCE: 11
caggagttga tcagcttgag aaaaatgccg aggaacgtc                            39

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: primer for
      sequencing of Escherichia coli fnr gene

<400> SEQUENCE: 12
gggtctagat tggtcgtcct ggttaggat                                      29

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: primer for
      sequencing of Escherichia coli sucA gene

<400> SEQUENCE: 13
cccaagcttc tgcccctgac actaagaca                                      29

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: primer for
      amplifying Escherichia coli sucA gene

<400> SEQUENCE: 14
cgaggtaacg ttcaagacct                                                 20

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: primer for
      amplifying Escherichia coli sucA gene

<400> SEQUENCE: 15
aggtcttgaa cgttacctcg atccataacg ggcagggcgc                           40

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: primer for
      amplifying Escherichia coli sucA gene

<400> SEQUENCE: 16
gggtctagac cactttgtca gtttcgatt                                       29

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: primer for
      amplifying Pantoea ananatis arcA gene

<400> SEQUENCE: 17
cccgaattcc ctgtttcgat ttagttggc                                       29

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence: primer for
      amplifying Pantoea ananatis arcA gene

<400> SEQUENCE: 18
cccgcatgcg attaatcttc cagatcacc                                       29

<210> SEQ ID NO 19
<211> LENGTH: 759
<212> TYPE: DNA
<213> ORGANISM: Pantoea ananatis
<220> FEATURE:
<221> NAME/KEY: CDS
<222> LOCATION: (41)..(757)

<400> SEQUENCE: 19
ccctgttttc aatttagttg gcaaaattag gtagctaaac atg cag acc ccg cac       55
                                            Met Gln Thr Pro His
                                              1               5
```

-continued

```
att ctc atc gtt gaa gac gaa ctg gtc acg cgc aat acc ctc aaa agc      103
Ile Leu Ile Val Glu Asp Glu Leu Val Thr Arg Asn Thr Leu Lys Ser
         10                  15                  20 att ttt gag gcg gaa ggt tat gtc gtg tac gaa gcg acc gat ggt gca      151
Ile Phe Glu Ala Glu Gly Tyr Val Val Tyr Glu Ala Thr Asp Gly Ala
     25                  30                  35 gag atg cac cag gtg ttg acc gac aat gat gtc aat ctg gtt att atg      199
Glu Met His Gln Val Leu Thr Asp Asn Asp Val Asn Leu Val Ile Met
         40                  45                  50 gac atc aat ctg ccg ggt aaa aac ggc ctg tta ctg gca cgt gaa ctg      247
Asp Ile Asn Leu Pro Gly Lys Asn Gly Leu Leu Leu Ala Arg Glu Leu
 55                  60                  65 cgt gag caa gcc aat gtc gca ttg atg ttc ctg acc gga cgc gat aac      295
Arg Glu Gln Ala Asn Val Ala Leu Met Phe Leu Thr Gly Arg Asp Asn
 70                  75                  80                  85 gaa gtc gat aaa att ctt ggg ctg gaa att ggt gca gac gac tac att      343
Glu Val Asp Lys Ile Leu Gly Leu Glu Ile Gly Ala Asp Asp Tyr Ile
             90                  95                 100 act aag ccg ttt aac cca cgc gaa tta act att cgt gca cgt aac ctg      391
Thr Lys Pro Phe Asn Pro Arg Glu Leu Thr Ile Arg Ala Arg Asn Leu
        105                 110                 115 ctg ttg cgc acc atg aat ttg cct tta ccc aat gaa gag cgt cgc cag      439
Leu Leu Arg Thr Met Asn Leu Pro Leu Pro Asn Glu Glu Arg Arg Gln
        120                 125                 130 gtt gaa agc tat aag ttc aac ggc tgg gag ctg gac atc aac agc cgc      487
Val Glu Ser Tyr Lys Phe Asn Gly Trp Glu Leu Asp Ile Asn Ser Arg
    135                 140                 145 tca ctc atc aat ccc aac ggt gag cag tac aaa ctg ccg cgc agt gag      535
Ser Leu Ile Asn Pro Asn Gly Glu Gln Tyr Lys Leu Pro Arg Ser Glu
150                 155                 160                 165 ttc cgt gcc atg ctg cac ttc tgc gaa aat ccc ggc aag att cag acg      583
Phe Arg Ala Met Leu His Phe Cys Glu Asn Pro Gly Lys Ile Gln Thr
                170                 175                 180 cgt gct gat ttg ctg aag aaa atg acc gga cgc gat ctc aag cca cac      631
Arg Ala Asp Leu Leu Lys Lys Met Thr Gly Arg Asp Leu Lys Pro His
            185                 190                 195 gac cgt act gtt gac gtg aca atc cgt cgt atc cgt aaa cat ttt gaa      679
Asp Arg Thr Val Asp Val Thr Ile Arg Arg Ile Arg Lys His Phe Glu
        200                 205                 210 tcc acg cca gat acc cct gaa atc atc gcc acc att cac ggc gaa ggt      727
Ser Thr Pro Asp Thr Pro Glu Ile Ile Ala Thr Ile His Gly Glu Gly
        215                 220                 225 tat cgt ttc tgt ggt gac ctg cag gat taa gc                          759
Tyr Arg Phe Cys Gly Asp Leu Gln Asp
```

<210> SEQ ID NO 20
<211> LENGTH: 238
<212> TYPE: PRT
<213> ORGANISM: Pantoea ananatis

<400> SEQUENCE: 20

```
Met Gln Thr Pro His Ile Leu Ile Val Glu Asp Glu Leu Val Thr Arg
 1               5                  10                  15

Asn Thr Leu Lys Ser Ile Phe Glu Ala Glu Gly Tyr Val Val Tyr Glu
             20                  25                  30

Ala Thr Asp Gly Ala Glu Met His Gln Val Leu Thr Asp Asn Asp Val
         35                  40                  45

Asn Leu Val Ile Met Asp Ile Asn Leu Pro Gly Lys Asn Gly Leu Leu
     50                  55                  60
```

```
Leu Ala Arg Glu Leu Arg Glu Gln Ala Asn Val Ala Leu Met Phe Leu
 65                  70                  75                  80

Thr Gly Arg Asp Asn Glu Val Asp Lys Ile Leu Gly Leu Glu Ile Gly
                 85                  90                  95

Ala Asp Asp Tyr Ile Thr Lys Pro Phe Asn Pro Arg Glu Leu Thr Ile
            100                 105                 110

Arg Ala Arg Asn Leu Leu Leu Arg Thr Met Asn Leu Pro Leu Pro Asn
        115                 120                 125

Glu Glu Arg Arg Gln Val Glu Ser Tyr Lys Phe Asn Gly Trp Glu Leu
    130                 135                 140

Asp Ile Asn Ser Arg Ser Leu Ile Asn Pro Asn Gly Glu Gln Tyr Lys
145                 150                 155                 160

Leu Pro Arg Ser Glu Phe Arg Ala Met Leu His Phe Cys Glu Asn Pro
                165                 170                 175

Gly Lys Ile Gln Thr Arg Ala Asp Leu Leu Lys Lys Met Thr Gly Arg
            180                 185                 190

Asp Leu Lys Pro His Asp Arg Thr Val Asp Val Thr Ile Arg Arg Ile
        195                 200                 205

Arg Lys His Phe Glu Ser Thr Pro Asp Thr Pro Glu Ile Ile Ala Thr
    210                 215                 220

Ile His Gly Glu Gly Tyr Arg Phe Cys Gly Asp Leu Gln Asp
225                 230                 235

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: primer for
      amplifying ori6K and mobRP4 gene

<400> SEQUENCE: 21
tcatagatct tttagattga tttatggtgc                                        30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: primer for
      amplifying ori6K and mobRP4 gene

<400> SEQUENCE: 22
ccacagatct aattcccatg tcagccgtta                                        30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence: primer for
      amplifying Chloramphenicol resistant gene

<400> SEQUENCE: 23
ataaagatct gtgtccctgt tgataccggg                                        30

<210> SEQ ID NO 24
<211> LENGTH: 30
<212> TYPE: DNA
<213> ORGANISM: Artificial Sequence
<220> FEATURE:
```

<223> OTHER INFORMATION: Description of Artificial Sequence: primer for
      amplifying Chloramphenicol resistant gene

<400> SEQUENCE: 24
ggggagatct tgcaaggcga ttaagttggg                            30

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: primer for
      amplifying kanamycin resistant gene

<400> SEQUENCE: 25
cccagatcta gttttcgccc cgaagaacg                             29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: primer for
      amplifying kanamycin resistant gene

<400> SEQUENCE: 26
cccagatctc cagagtcccg ctcagaaga                             29

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: primer for
      amplifying Pantoea ananatis arcA gene

<400> SEQUENCE: 27
cccgaattcg cgaccgatgg tgcagagat                             29

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: primer for
      amplifying Pantoea ananatis arcA gene

<400> SEQUENCE: 28
aaggcaaatt catggtgcgc                                       20

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: primer for
      amplifying Pantoea ananatis arcA gene

<400> SEQUENCE: 29
gcgcaccatg aatttgcctt acccaatgaa gagcgtcgcc                 40

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: primer for -continued amplifying Pantoea ananatis arcA gene

<400> SEQUENCE: 30
cccgcatgca ccttcgccgt gaatggtgg                              29

<210> SEQ ID NO 31
<211> LENGTH: 927
<212> TYPE: DNA
<213> ORGANISM: Escherichia coli
<220> FEATURE:
<221> NAME/KEY: CDS
<222> LOCATION: (101)..(817)

<400> SEQUENCE: 31

```
gtcatgttac gccgatcatg ttaatttgca gcatgcatca ggcaggtcag ggacttttgt      60
acttcctgtt tcgatttagt tggcaattta ggtagcaaac atg cag acc ccg cac      115
                                             Met Gln Thr Pro His
                                               1               5 att ctt atc gtt gaa gac gag ttg gta aca cgc aac acg ttg aaa agt      163
Ile Leu Ile Val Glu Asp Glu Leu Val Thr Arg Asn Thr Leu Lys Ser
            10                  15                  20 att ttc gaa gcg gaa ggc tat gat gtt ttc gaa gcg aca gat ggc gcg      211
Ile Phe Glu Ala Glu Gly Tyr Asp Val Phe Glu Ala Thr Asp Gly Ala
        25                  30                  35 gaa atg cat cag atc ctc tct gaa tat gac atc aac ctg gtg atc atg      259
Glu Met His Gln Ile Leu Ser Glu Tyr Asp Ile Asn Leu Val Ile Met
    40                  45                  50 gat atc aat ctg ccg ggt aag aac ggt ctt ctg tta gcg cgt gaa ctg      307
Asp Ile Asn Leu Pro Gly Lys Asn Gly Leu Leu Leu Ala Arg Glu Leu
55                  60                  65 cgc gag cag gcg aat gtt gcg ttg atg ttc ctg act ggc cgt gac aac      355
Arg Glu Gln Ala Asn Val Ala Leu Met Phe Leu Thr Gly Arg Asp Asn
70                  75                  80                  85 gaa gtc gat aaa att ctc ggc ctc gaa atc ggt gca gat gac tac atc      403
Glu Val Asp Lys Ile Leu Gly Leu Glu Ile Gly Ala Asp Asp Tyr Ile
                90                  95                 100 acc aaa ccg ttc aac ccg cgt gaa ctg acg att cgt gca cgc aac cta      451
Thr Lys Pro Phe Asn Pro Arg Glu Leu Thr Ile Arg Ala Arg Asn Leu
            105                 110                 115 ctg tcc cgt acc atg aat ctg ggt act gtc agc gaa gaa cgt cgt agc      499
Leu Ser Arg Thr Met Asn Leu Gly Thr Val Ser Glu Glu Arg Arg Ser
        120                 125                 130 gtt gaa agc tac aag ttc aat ggt tgg gaa ctg gac atc aac agc cgt      547
Val Glu Ser Tyr Lys Phe Asn Gly Trp Glu Leu Asp Ile Asn Ser Arg
    135                 140                 145 tcg ttg atc ggc cct gat ggc gag cag tac aag ctg ccg cgc agc gag      595
Ser Leu Ile Gly Pro Asp Gly Glu Gln Tyr Lys Leu Pro Arg Ser Glu
150                 155                 160                 165 ttc cgc gcc atg ctt cac ttc tgt gaa aac cca ggc aaa att cag tcc      643
Phe Arg Ala Met Leu His Phe Cys Glu Asn Pro Gly Lys Ile Gln Ser
                170                 175                 180 cgt gct gaa ctg ctg aag aaa atg acc ggc cgt gag ctg aaa ccg cac      691
Arg Ala Glu Leu Leu Lys Lys Met Thr Gly Arg Glu Leu Lys Pro His
            185                 190                 195 gac cgt act gta gac gtg acg atc cgc cgt att cgt aaa cat ttc gaa      739
Asp Arg Thr Val Asp Val Thr Ile Arg Arg Ile Arg Lys His Phe Glu
        200                 205                 210 tct acg ccg gat acg ccg gaa atc atc gcc acc att cac ggt gaa ggt      787
Ser Thr Pro Asp Thr Pro Glu Ile Ile Ala Thr Ile His Gly Glu Gly
    215                 220                 225
```

```
tat cgc ttc tgc ggt gat ctg gaa gat taa tcggctttac caccgtcaaa      837
Tyr Arg Phe Cys Gly Asp Leu Glu Asp
230                 235 aaaaacggcg ctttttagcg ccgtttttat ttttcaacct tatttccaga tacgtaactc   897
atcgtccgtt gtaacttctt tactggcttt                                   927

<210> SEQ ID NO 32
<211> LENGTH: 238
<212> TYPE: PRT
<213> ORGANISM: Escherichia coli

<400> SEQUENCE: 32

Met Gln Thr Pro His Ile Leu Ile Val Glu Asp Glu Leu Val Thr Arg
 1               5                  10                  15

Asn Thr Leu Lys Ser Ile Phe Glu Ala Glu Gly Tyr Asp Val Phe Glu
                20                  25                  30

Ala Thr Asp Gly Ala Glu Met His Gln Ile Leu Ser Glu Tyr Asp Ile
            35                  40                  45

Asn Leu Val Ile Met Asp Ile Asn Leu Pro Gly Lys Asn Gly Leu Leu
        50                  55                  60

Leu Ala Arg Glu Leu Arg Glu Gln Ala Asn Val Ala Leu Met Phe Leu
65                  70                  75                  80

Thr Gly Arg Asp Asn Glu Val Asp Lys Ile Leu Gly Leu Glu Ile Gly
                85                  90                  95

Ala Asp Asp Tyr Ile Thr Lys Pro Phe Asn Pro Arg Glu Leu Thr Ile
            100                 105                 110

Arg Ala Arg Asn Leu Leu Ser Arg Thr Met Asn Leu Gly Thr Val Ser
        115                 120                 125

Glu Glu Arg Arg Ser Val Glu Ser Tyr Lys Phe Asn Gly Trp Glu Leu
    130                 135                 140

Asp Ile Asn Ser Arg Ser Leu Ile Gly Pro Asp Gly Glu Gln Tyr Lys
145                 150                 155                 160

Leu Pro Arg Ser Glu Phe Arg Ala Met Leu His Phe Cys Glu Asn Pro
                165                 170                 175

Gly Lys Ile Gln Ser Arg Ala Glu Leu Leu Lys Lys Met Thr Gly Arg
            180                 185                 190

Glu Leu Lys Pro His Asp Arg Thr Val Asp Val Thr Ile Arg Arg Ile
        195                 200                 205

Arg Lys His Phe Glu Ser Thr Pro Asp Thr Pro Glu Ile Ile Ala Thr
    210                 215                 220

Ile His Gly Glu Gly Tyr Arg Phe Cys Gly Asp Leu Glu Asp
225                 230                 235
```